US008225793B2

(12) United States Patent
Chang

(10) Patent No.: US 8,225,793 B2
(45) Date of Patent: Jul. 24, 2012

(54) RESPIRATORY MASK DEVICE HAVING IMPROVED HEAD STRAP CONNECTORS

(75) Inventor: Eric Chang, Taichung Hsien (TW)

(73) Assignee: Hsiner Co., Ltd., Taichung Hsien (TW)

( * ) Notice: Subject to any disclaimer, the term of this patent is extended or adjusted under 35 U.S.C. 154(b) by 252 days.

(21) Appl. No.: 12/779,028

(22) Filed: May 12, 2010

(65) Prior Publication Data

US 2011/0277770 A1 Nov. 17, 2011

(51) Int. Cl.
*A61M 11/00* (2006.01)

(52) U.S. Cl. ......... 128/206.21; 128/201.28; 128/207.11; 128/207.13

(58) Field of Classification Search ............ 128/206.21, 128/201.28, 207.11, 207.13, 206.24, 206.27, 128/206.28
See application file for complete search history.

(56) References Cited

U.S. PATENT DOCUMENTS

| 7,100,610 B2* | 9/2006 | Biener et al. ............ 128/206.21 |
| 7,207,335 B2* | 4/2007 | Kwok et al. ............ 128/207.12 |
| 7,568,483 B2* | 8/2009 | Scarberry et al. ........ 128/206.21 |
| 7,845,352 B2* | 12/2010 | Sleeper et al. ........... 128/206.23 |
| 8,051,855 B2* | 11/2011 | Ho et al. ................ 128/206.21 |
| 2005/0056286 A1* | 3/2005 | Huddart et al. .......... 128/206.21 |
| 2007/0215161 A1 | 9/2007 | Frater et al. |

FOREIGN PATENT DOCUMENTS

| WO | WO 2006/074515 | 7/2006 |
| WO | WO 2006/138416 | 12/2006 |
| WO | WO 2007/048174 | 5/2007 |
| WO | WO 2009/108995 | 9/2009 |

OTHER PUBLICATIONS

Combined Search and Examination report dated Aug. 20, 2010 and issued in connection with the corresponding U.K. Appln. No. GB1007909.3.

* cited by examiner

*Primary Examiner* — Steven Douglas
(74) *Attorney, Agent, or Firm* — DLA Piper LLP (US)

(57) ABSTRACT

A respiratory mask device includes a mask body that has a front gas inlet and a rear abutment end to contact a patient's face, left and right upper connectors disposed on left and right sides of the front gas inlet for connection with an upper head strap, left and right lower connectors respectively disposed beneath the left and right upper connectors, and left and right cantilever arms fixed at a top side of the mask body. The left and right cantilever arms extend downward and sideward from the top side and have bottom free ends carrying respective left and right upper connectors. With the cantilever arms, pulling forces can be dispersed uniformly on the mask body, and uncomfortable pressure experienced by a user may be eliminated.

9 Claims, 14 Drawing Sheets

RESPIRATORY MASK DEVICE HAVING IMPROVED HEAD STRAP CONNECTORS

BACKGROUND OF THE INVENTION

1. Field of the Invention

The invention relates to a respiratory mask device, more particularly, to a respiratory mask device having cantilever arms carrying head strap connectors.

2. Description of the Related Art

It is known to use respiratory masks, such as nasal masks, face masks, etc., for treatment of various respiratory conditions such as obstructive sleep apnea. When a respiratory mask is used, the respiratory mask is placed over the nose, or the nose and mouth of a patient and is held to the head of the patient using a head strap connected to the respiratory mask. When the head strap is tightened on the patent's head, the head strap pulls the respiratory mask to abut against the patient's face, thereby holding the respiratory mask in place. Generally, in order to stabilize the respiratory mask, pulling forces are applied to two points at left and right sides of the patient's nose, and to another two points substantially at left and right sides of the upper lip of the patient.

Referring to FIGS. 1 and 2, there is shown a respiratory mask device 1 disclosed in Taiwanese Patent Application No. 94111323, which is connected to a gas supply device 11. The respiratory mask device 1 includes a mask body 12 used to cover the nose and mouth of a patient, two upper connectors 13, two lower connectors 14, two upper head straps 15 connected respectively to the upper connectors 13, and two lower head straps 15 connected to the lower connectors 14. The mask body 12 can be held in place by fastening the upper and lower head straps 15 to the head of the patient. However, the following disadvantages are encountered by the respiratory mask device 1.

1. Because the upper connectors 13 are disposed at left and right sides of the patient's nose, when the upper head straps 15 are pulled rearward, the upper head straps 15 tend to cover parts of the patient's eyes, thereby causing discomfort to the patient.

2. Although the positions of the upper connectors 13 may be lowered slightly to change the position of the upper head straps 15 or to prevent the upper straps 15 from covering the patient's eyes, if the upper connectors 13 are lowered, they will become closer to the lower connectors 14, concentrating the points of application of pulling forces at the lower part of the mask body 12. As a result, the mask body 12 will become unbalanced and unstable, and the upper head straps 15 may exert uncomfortable pressure on part of the patient's ears.

Referring to FIG. 3, another respiratory mask device 2 in the prior art includes a mask body 21, two lower connectors 22 respectively connected to two lower head straps 24, and an extension strap 23 extending upwardly from the mask body 21 and having two upper connectors 232 which are connected respectively to two upper head straps 24. In this respiratory mask device, although the lower connectors 22 and the lower head straps 24 can balance the lower part of the mask body 21 and prevent the same from tilting leftward and rightward, because the upper connectors 232 are connected to the single extension strap 23, the upper part of the mask body 21 may tilt when subjected to an external force. In addition, because the extension strap 23 extends between the eyes of the patient, it May interfere with the patient's vision and cause inconveniences.

SUMMARY OF THE INVENTION

Therefore, the main object of the present invention is to provide a respiratory mask device that can be positioned stably to the face of a patient without causing discomfort to the patient.

Accordingly, the present invention provides a respiratory mask device which comprises: a mask body including a front gas inlet, a rear abutment end adapted to contact a patient's face, left and right upper connectors respectively disposed on left and right sides of the front gas inlet, left and right lower connectors respectively disposed beneath the left and right upper connectors, and left and right cantilever arms fixed at a top side of the mask body and disposed between the front gas inlet and the rear abutment end. The left cantilever arm extends downward and leftward from a top side of the mask body and has a bottom free end carrying the left upper connector. The right cantilever arm extends downward and rightward from the top side of the mask body and has a bottom free end carrying the right upper connector; a lower head strap connected to the left and right lower connectors; and an upper head strap connected to the left and right upper connectors.

BRIEF DESCRIPTION OF THE DRAWINGS

Other features and advantages of the present invention will become apparent in the following detailed description of the preferred embodiments with reference to the accompanying drawings, of which.

DETAILED DESCRIPTION OF THE PREFERRED EMBODIMENTS

Figure 1:
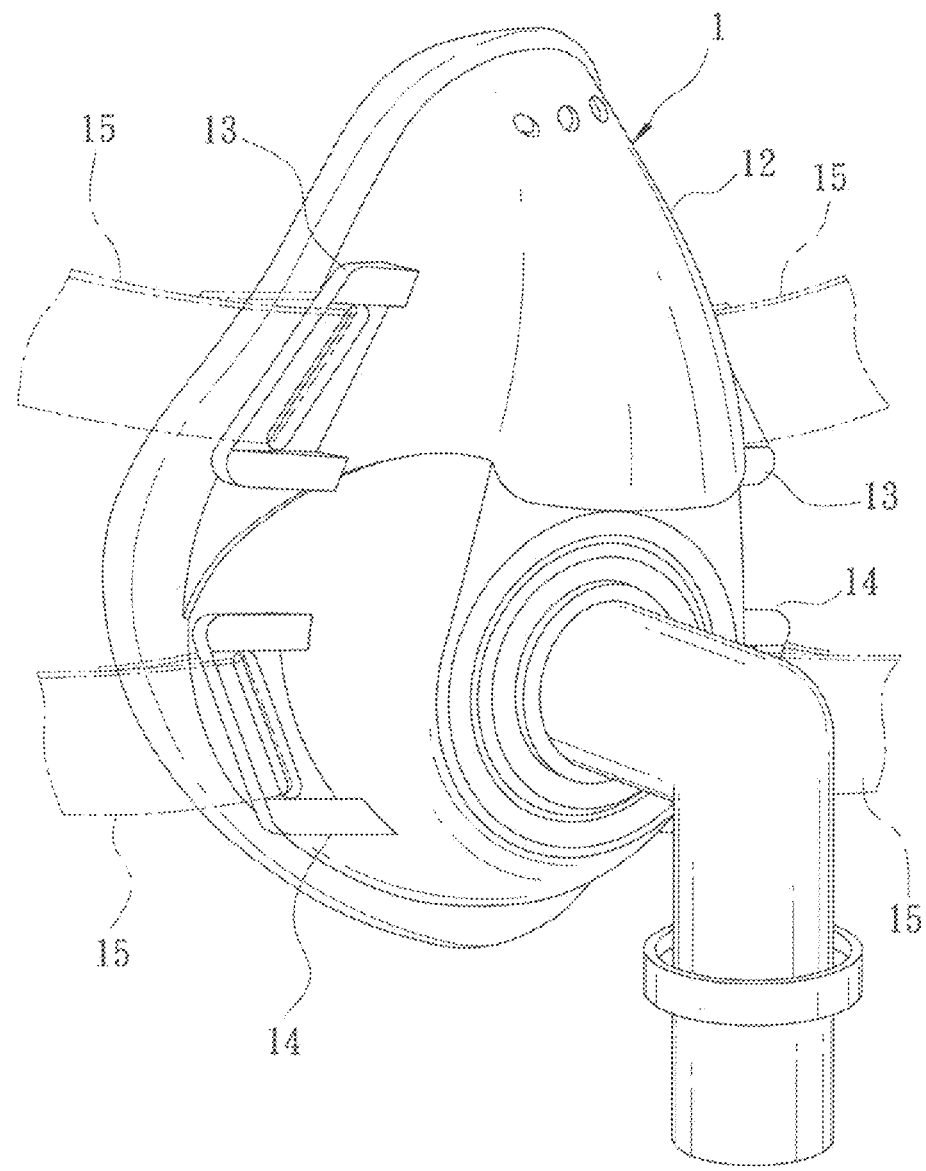
FIGS. 1 and 2 show a: conventional respiratory mask device.
Figure 2:
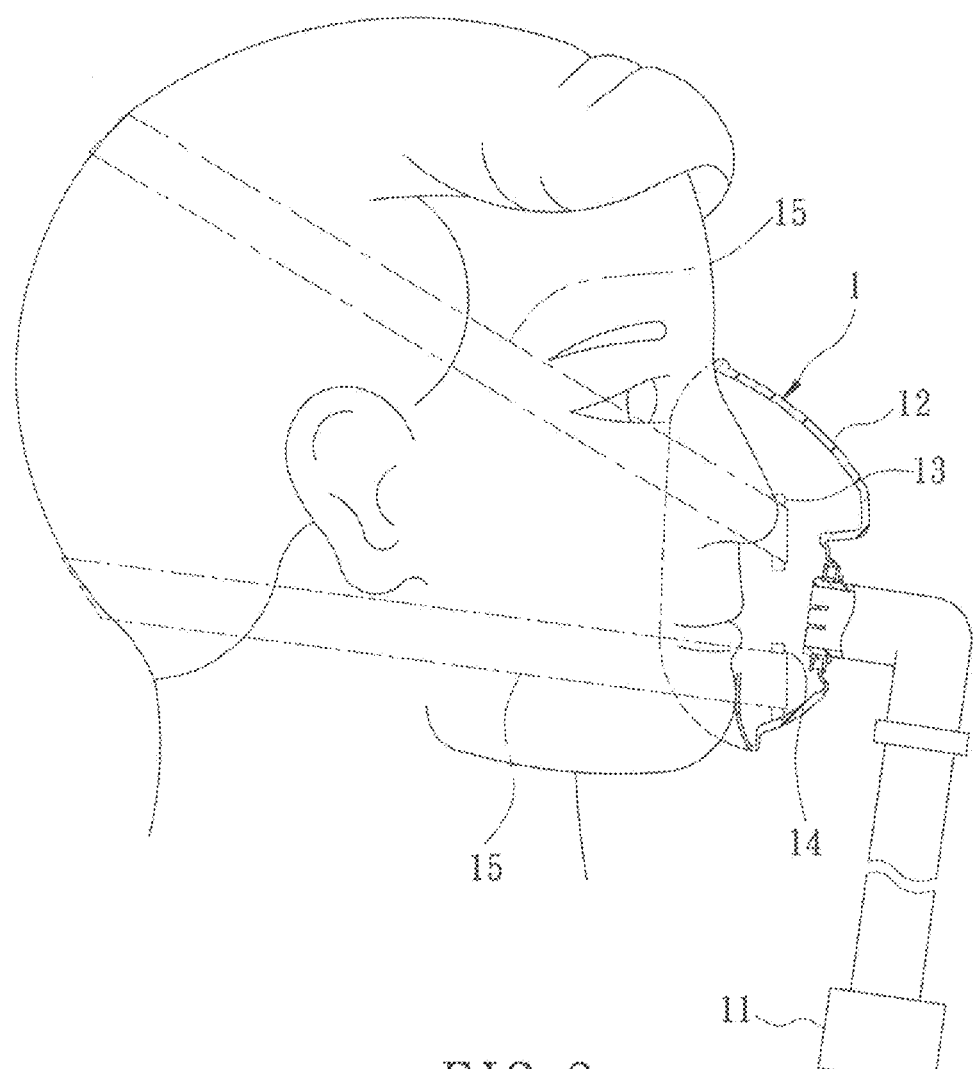
Figure 3:
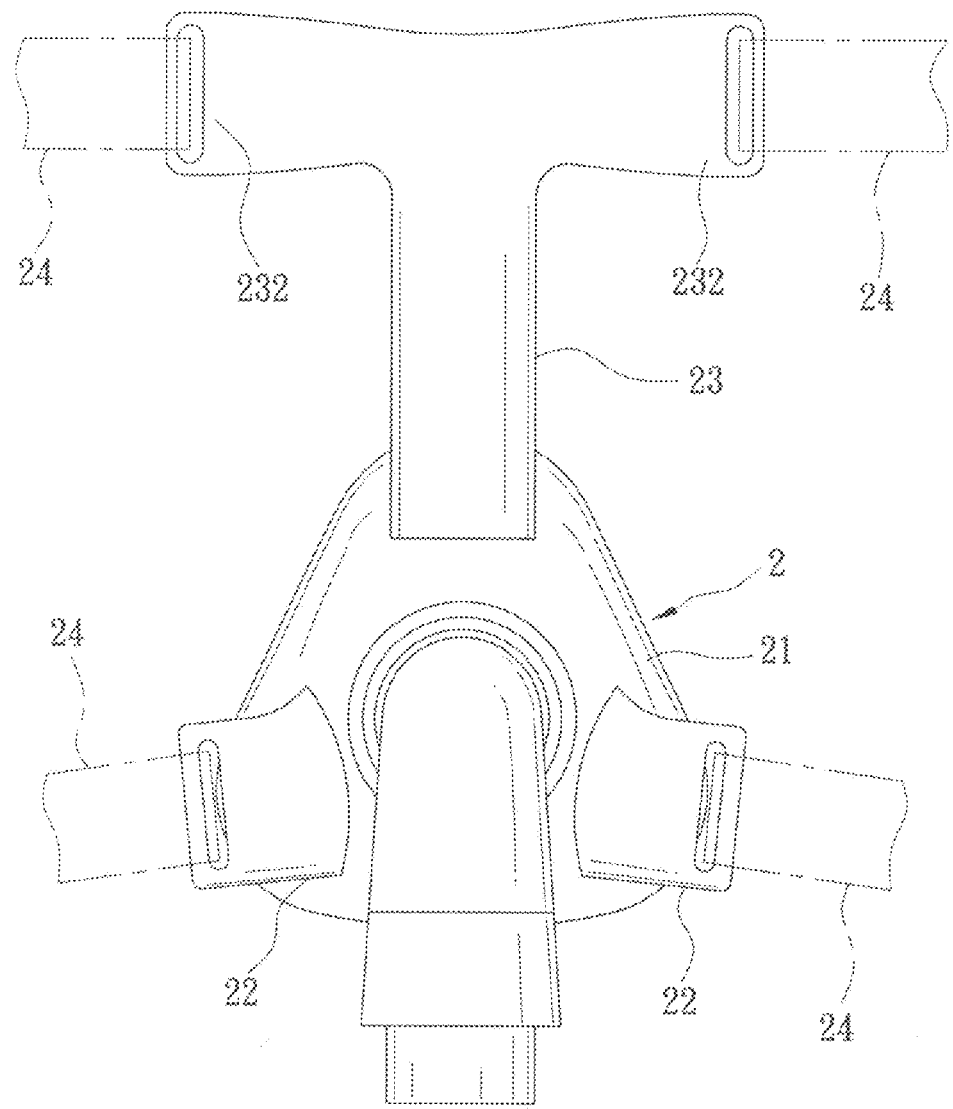
FIG. 3 shows another conventional respiratory mask device.

Before the present invention is described in greater detail with reference to the accompanying preferred embodiments, it should be noted herein that like elements are denoted by the same reference numerals throughout the disclosure.

Figure 4:
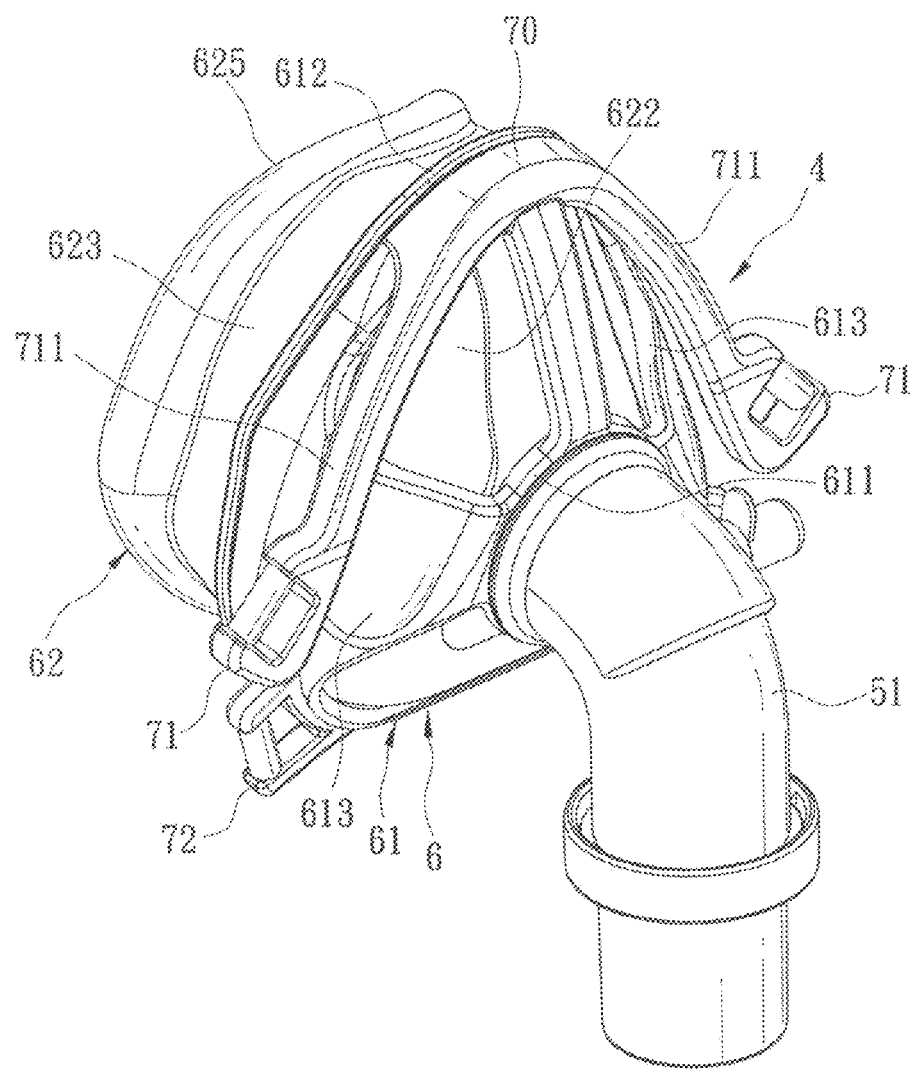
FIG. 4 is a perspective view of a respiratory mask device according to the first preferred embodiment of the present invention.
Figure 5:
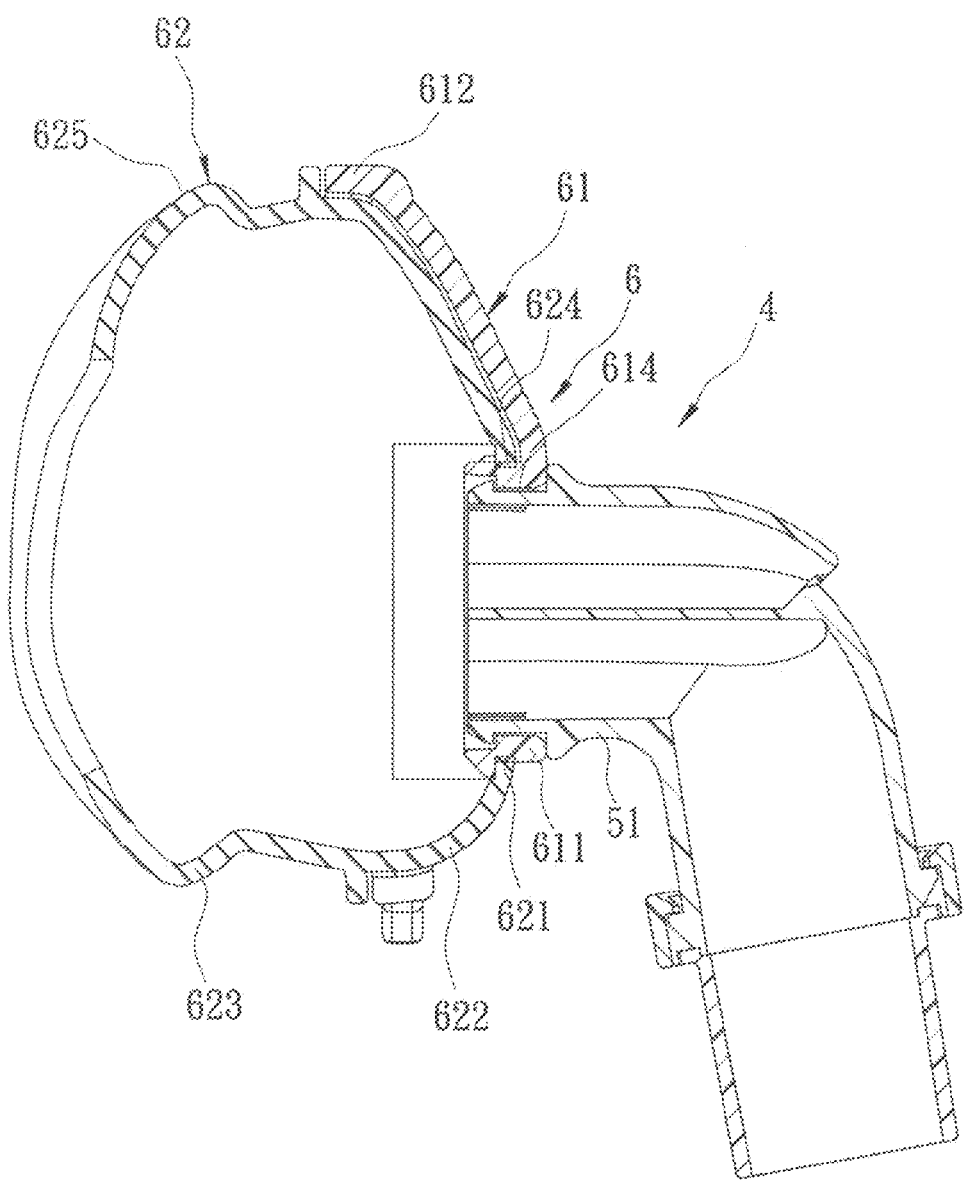
FIG. 5 is a sectional view of the respiratory mask device of FIG. 4.
Figure 6:
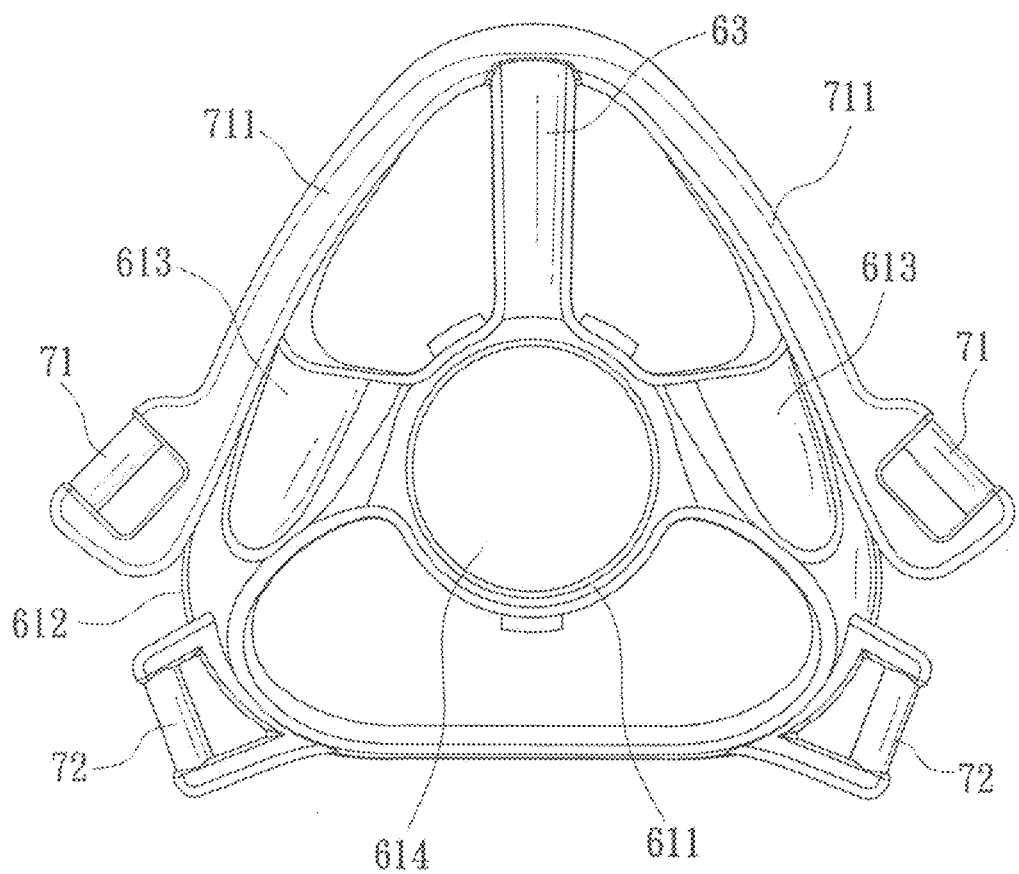
FIG. 6 is a front view of a support frame of the respiratory mask device of FIG. 4.
Figure 7:
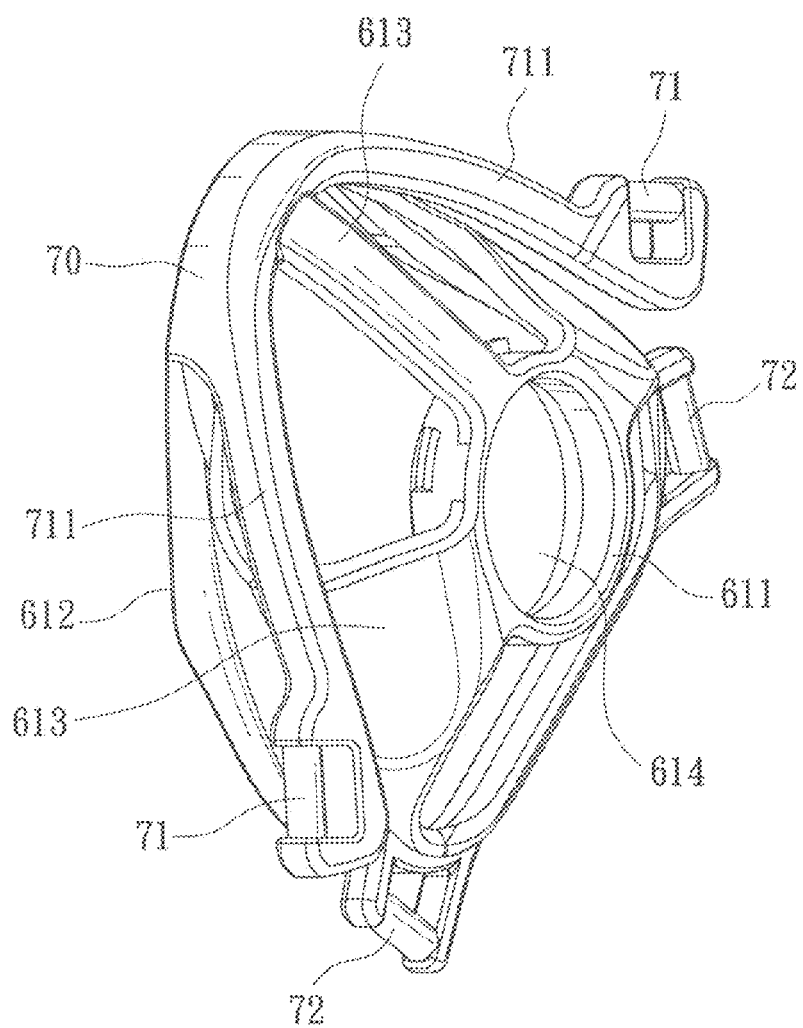
FIG. 7 is a perspective view of the support frame of FIG. 6.
Figure 8:
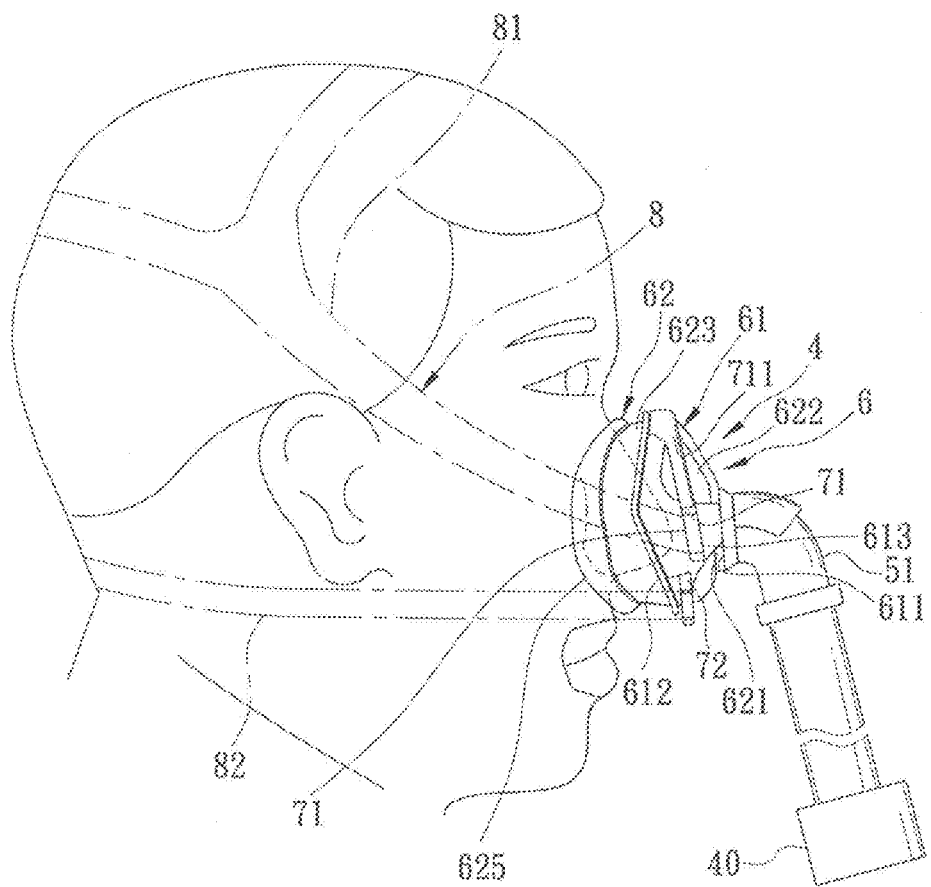
FIG. 8 is a side view showing the respiratory mask device of FIG. 4 in use.
Figure 9:
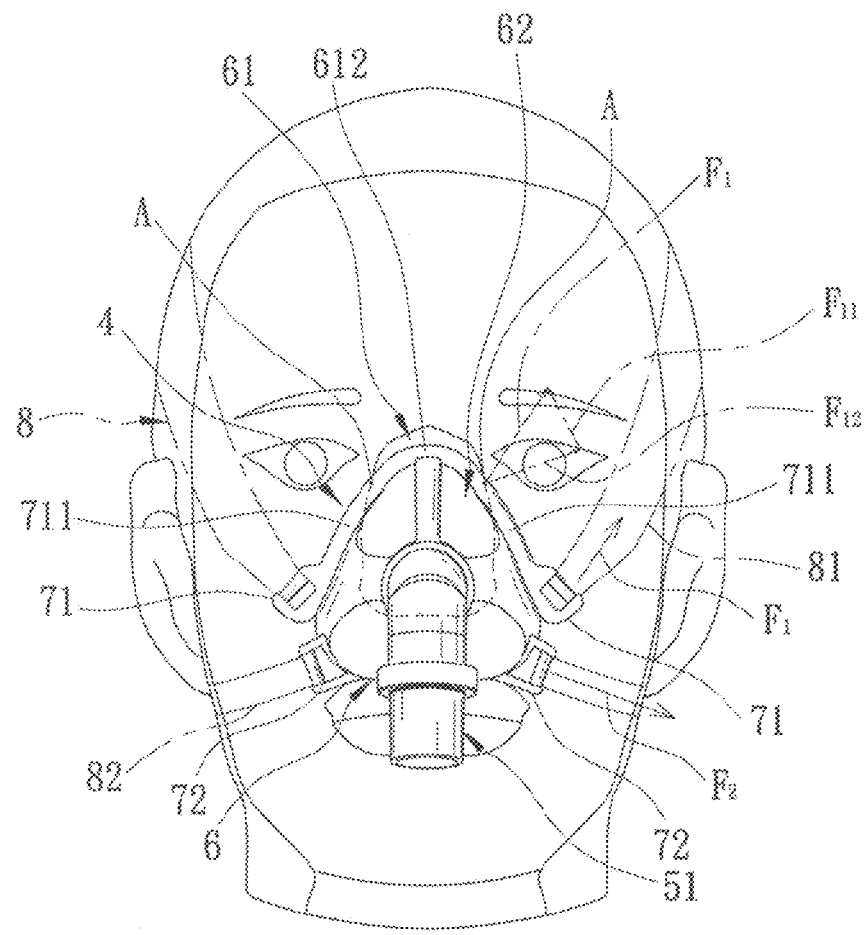
FIG. 9 is a front view showing the respiratory mask device of FIG. 4 in use.

Referring to FIGS. 4-9, there is shown a respiratory mask device 4 according to the first preferred embodiment of the present invention, which includes a gas supply 40, a gas inlet tube 51 connected to the gas supply 40, a mask body 6 connected to the gas inlet tube 51, and a head strap unit 8.

The mask body 6 includes a support frame 61, and a shell 62 fitted to the support frame 61. The support frame 61 has a rim member 612, a front annular member 611 defining an opening 614 in front of the rim member 612, and a plurality of frame members 613 extending forwardly and convergingly from the rim member 612 to the front annular member 611 to interconnect the rim member 612 and the front annular member 611.

The shell 62 is a soft shell and includes a front shell portion 622 disposed within the support frame 61 in abutment with the rim member 612 and the frame members 613, and a rear shell portion 623 extending rearwardly and outwardly from the support frame 61. The front shell portion 622 has a front open end 621 that defines a front gas inlet 624 in alignment with the opening 614 of the front annular member 611 of the support frame 61 and that is fitted around the front annular member 611 of the support frame 61. The rear shell portion 623 has a rear abutment end 625 adapted to contact a patient's face.

The support frame 61 further includes left and right upper connectors 71 that are disposed respectively on left and right sides of the front annular member 611, and left and right lower connectors 72 disposed beneath the left and right upper connectors 71, respectively. Left and right cantilever arms 711 are fixed at a top side of the mask body 6 and are disposed between the front annular member 611 of the support frame 61 and the rear abutment end 625 of the rear shell portion 62. The left and right cantilever arms 711 are integral with a top plate 70 that has a rear end fixed to a top side of the rim member 612 and that projects forwardly from the top side of the rim member 612. The left cantilever arm 711 extends downward and leftward from the top plate 70 and has a bottom free end carrying the left upper connector 71. The right cantilever arm 711 extends downward and rightward from the top plate 70 and has a bottom free end carrying the right upper connector 71. The left and right cantilever arms 711 are substantially symmetrical with respect to a plane that divides symmetrically the top plate 70 and the front annular member 611.

The head strap unit 8 has an upper head strap 81 connected to the left and right upper connectors 71, and a lower head strap 82 connected to the left and right lower connectors 72.

Referring once again to FIG. 9, in use, the mask body 6 is placed over the nose of a patient, and the upper and lower head straps 81 and 82 are put around the head of the patient. When the upper and lower head straps 81, 82 are pulled rearward, pulling forces (F1) are exerted on the left and right upper connectors 71, and pulling forces (F2) are exerted on the left and right lower connectors 72. The pulling forces (F2) are transferred to the lower part of the rim member 612 of the support frame 61. The pulling forces (F1) are transferred to the upper part of the rim member 612 although the positions of the left and right upper connectors 71 are proximate to the left and right lower connectors 72. This is because the left and right cantilever arms 711 which carry the left and right upper connectors 71 are fixed to the top plate 70 disposed at the top side of the rim member 612 of the support frame 61, and the pulling forces (F1) applied to the left and right upper connectors 71 are transferred to the top side of the rim member 612 through two fixed points (A) of the left and right cantilever arms 711 on the top plate 70. Therefore, the pulling forces (F1, F2) are not concentrated at the lower part of the mask body 6. The arrangement of the left and right cantilever arms 711 permits the upper connectors 71 to be lowered toward the lower connectors 72 so that the upper head straps 81 will not interfere with the patient's eyes.

In addition, because the pulling force (F1) exerted on each fixed point (A) will be divided into an upward force component (F11) and a rearward force component (F12), the pulling forces (F1) are dispersed when transferred to the rim member 612. Therefore, the pulling forces may be exerted evenly on the support frame 61, and the mask body 6 can be stabilized on the nose of the patient without causing discomfort to the patient.

Moreover, the upper connectors 71 are movable resiliently because they are provided on the cantilever arms 711. Accordingly, the upper head straps 81 will not cause uncomfortable pressure on the patient's head, particularly, on the patient's ears, when the upper head straps 81 are lowered for adjustment.

Figure 10:
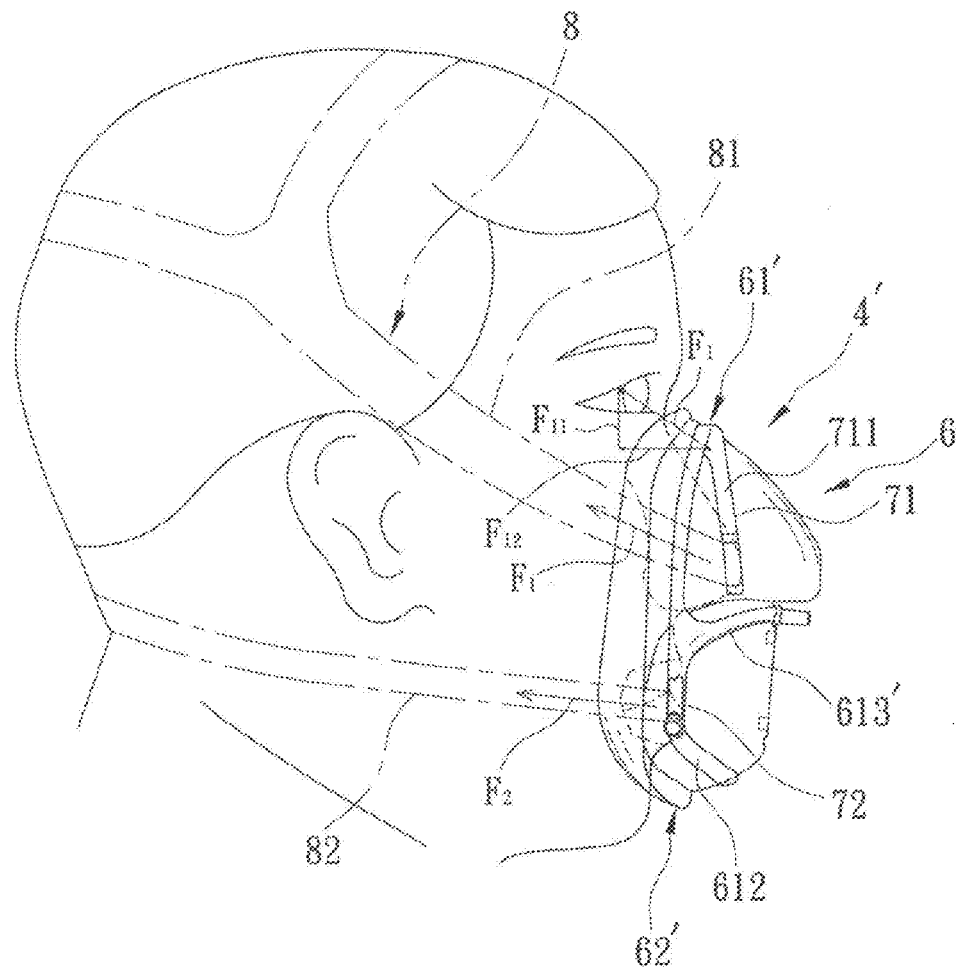
FIG. 10 is a side view of a respiratory mask device according to the second preferred embodiment of the present invention in use.
Figure 11:
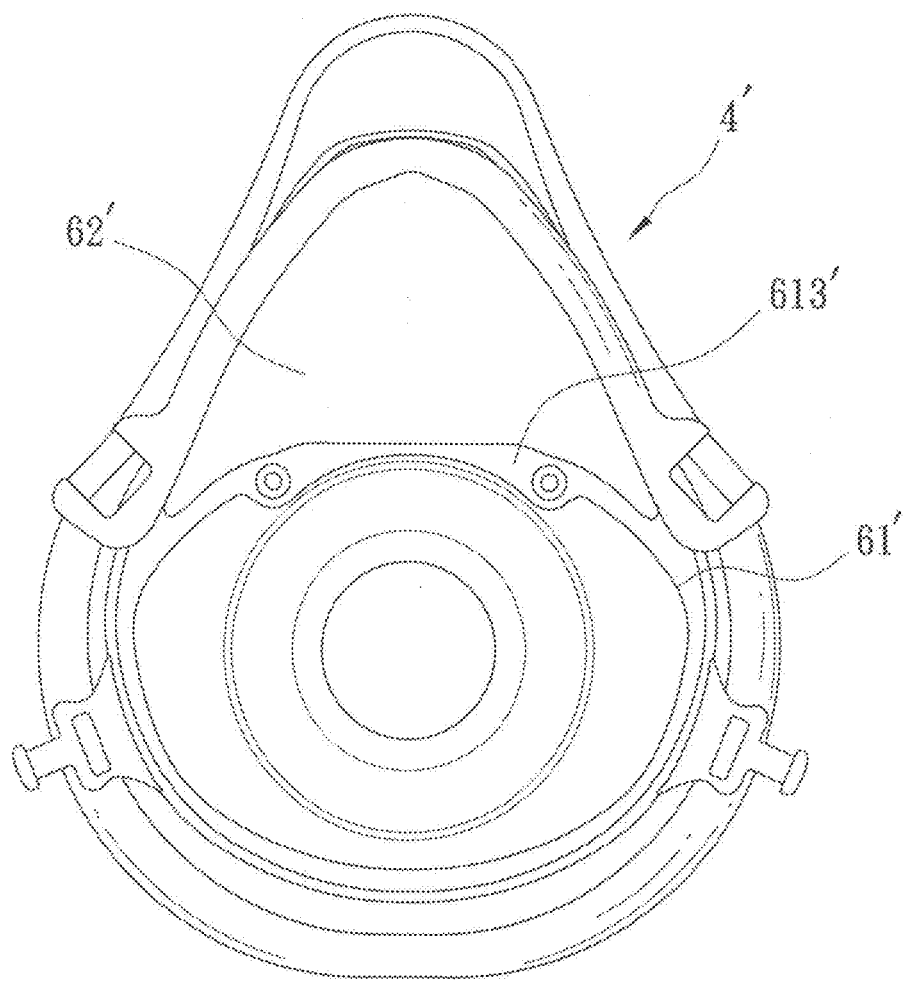
FIG. 11 is a front view of the respiratory mask device of FIG. 10.
Figure 12:
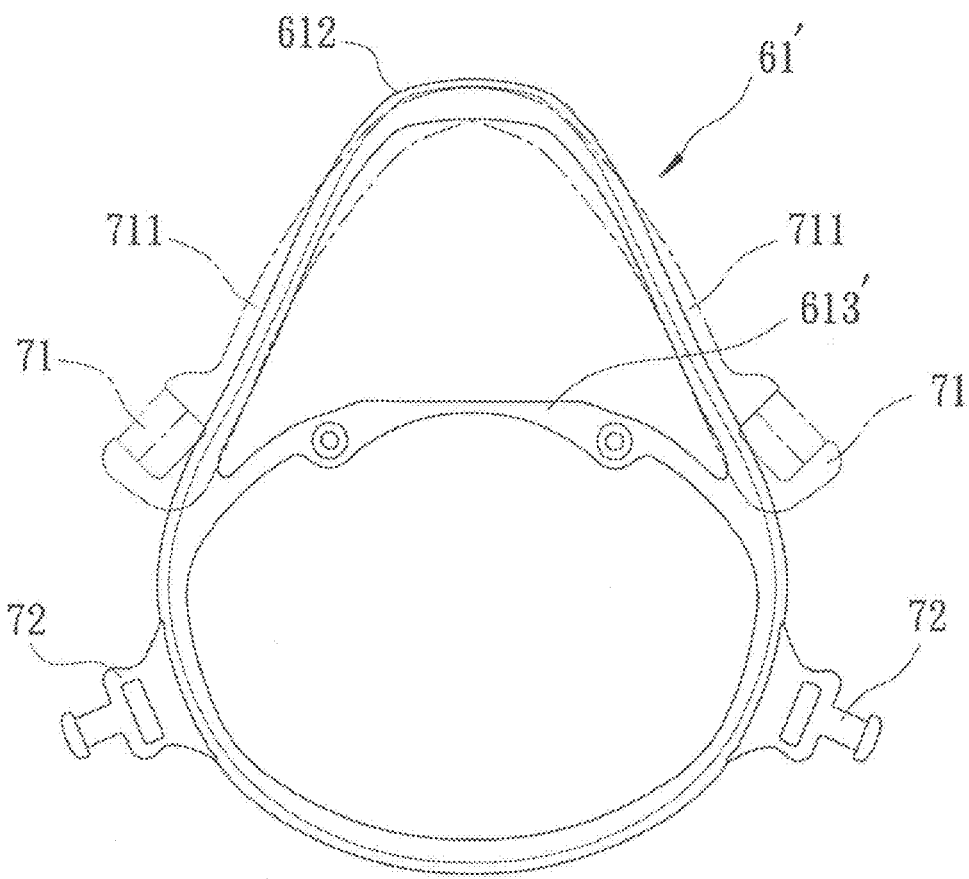
FIG. 12 is a front view of the support frame of the respiratory mask device of FIG. 10.
Figure 13:
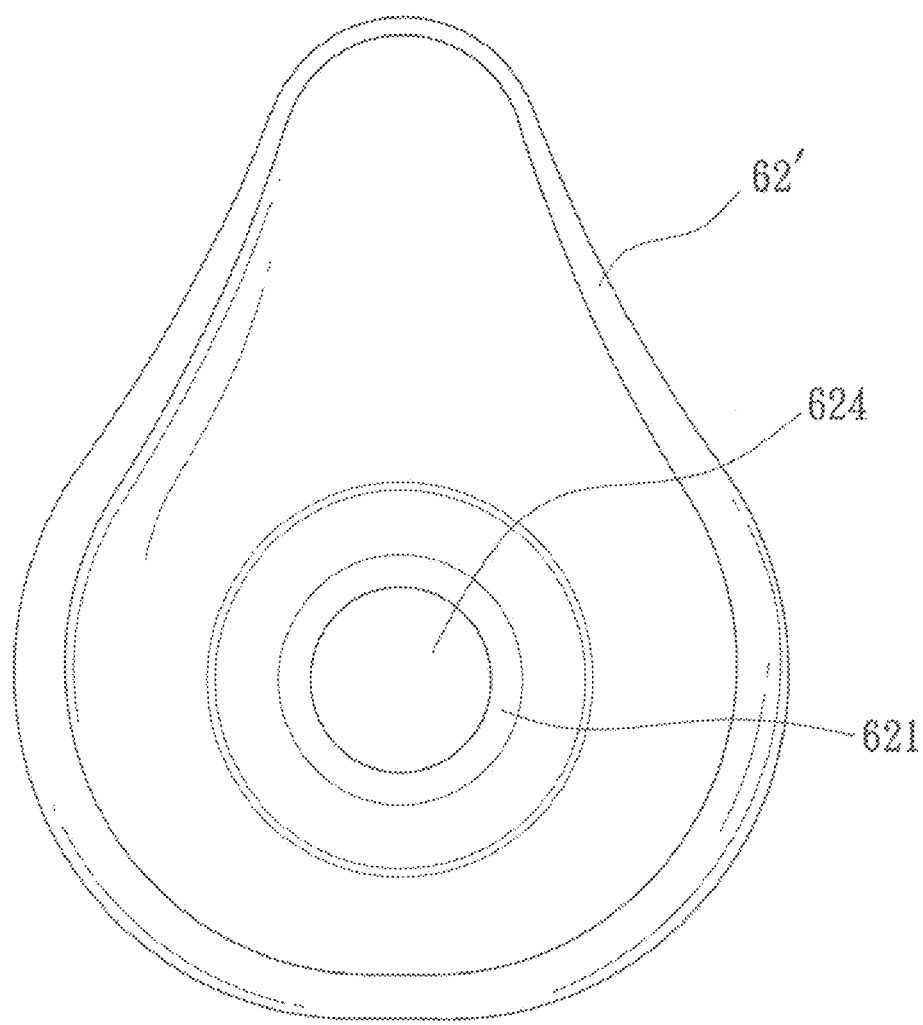
FIG. 13 is a front view of a shell of the respiratory mask device of FIG. 10.
Figure 14:
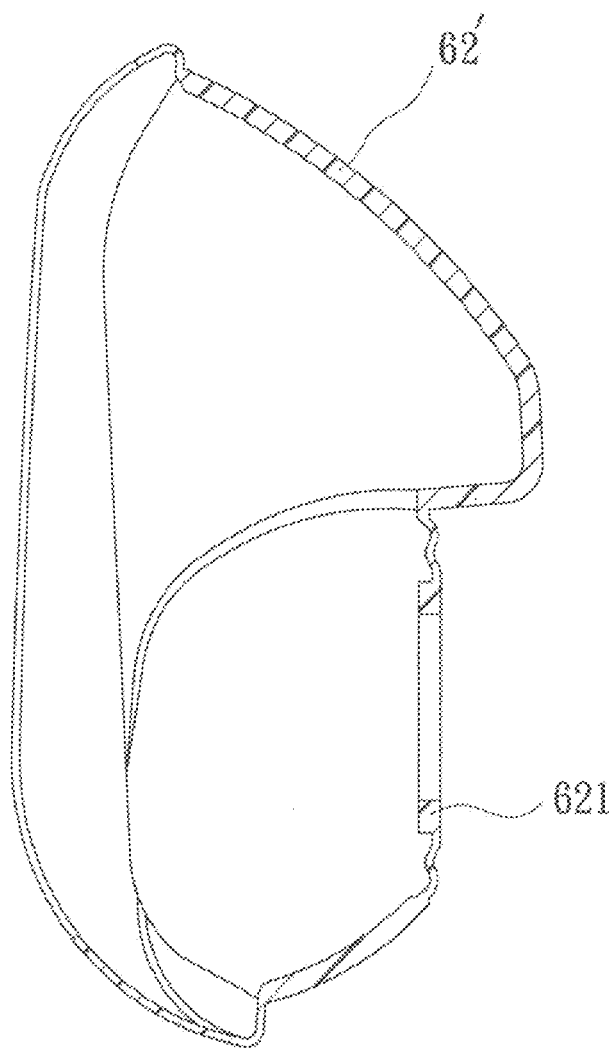
FIG. 14 is a side view of the shell of the respiratory mask device of FIG. 13.

Referring to FIGS. 10-14, there is shown a respiratory mask device 4' according to the second preferred embodiment of the present invention. The respiratory mask device 4' includes a support frame 61' and a shell 62' fitted to the support frame 61'. Like the support frame 61 of the first preferred embodiment, the support frame 61' has left and right cantilever arms 711 that have bottom free ends respectively holding left and right upper connectors 71 and that are fixed to a top side of a rim member 612 that is disposed around the shell 62'. A frame member 613' spans the rim member 612 and projects forwardly to the front open end 621 that defines the front gas inlet 624 of the shell 62'. However, the respiratory mask device 4' in this embodiment is used to cover the nose and mouth of the patient.

While the present invention has been described in connection with what is considered the most practical and preferred embodiments, it is understood that this invention is not limited to the disclosed embodiments but is intended to cover various arrangements included within the spirit and scope of the broadest interpretation so as to encompass all such modifications and equivalent arrangements.

What is claimed is:

1. A respiratory mask device comprising:
   a mask body including a front gas inlet, a rear abutment end adapted to contact a patient's face, left and right upper connectors respectively disposed on left and right sides of said front gas inlet, left and right lower connectors respectively disposed beneath said left and right upper connectors, and left and right cantilever arms fixed at a top side of said mask body and disposed between said front gas inlet and said rear abutment end, said left cantilever arm extending downward and leftward from a top side of said mask body and having a bottom free end carrying said left upper connector, said right cantilever arm extending downward and rightward from said top side of said mask body and having a bottom free end carrying said right upper connector;
   a lower head strap connected to said left and right lower connectors; and
   an upper head strap connected to said left and right upper connectors.

2. The respiratory mask device of claim 1, wherein said left and right cantilever arms are substantially symmetrical and are interconnected at said top side of said mask body.

3. The respiratory mask device of claim 1, wherein said mask body further includes a support frame having said left and right cantilever arms, and a shell fitted to said support frame and having said front gas inlet and said rear abutment end.

4. The respiratory mask device of claim 3, wherein said support frame further has a rim member extending around said shell between said front gas inlet and said rear abutment end, said left and right cantilever arms being fixed to a top side of said rim member.

5. The respiratory mask device of claim 4, wherein said shell further has a front open end in front of said rim member to confine said front gas inlet.

6. The respiratory mask device of claim 5, wherein said support frame further has a front annular member that defines an opening aligned with said front gas inlet, said front open end and said front annular member being fitted to each other.

7. The respiratory mask device of claim 6, wherein said support frame further has a plurality of spaced apart frame members extending forwardly and convergingly from said rim member to said front annular member to interconnect said rim member and said front annular member.

8. The respiratory mask device of claim 7, said shell includes a front shell portion disposed within said support frame in abutment with said rim member and said frame members, and a rear shell portion extending out of said support frame.

9. The respiratory mask device of claim 4, wherein said support frame further a top plate that has a rear end connected to said top side of said rim member and that projects forwardly from said top side of said rim member, said left and right cantilever arms being fixed to said top plate.

* * * * *